(12) United States Patent
Shirahase et al.

(10) Patent No.: US 7,148,063 B2
(45) Date of Patent: Dec. 12, 2006

(54) MITOCHONDRIAL CREATINE KINASE ANTIBODY

(75) Inventors: Yasushi Shirahase, Kobe (JP); Tadahiro Kajita, Kobe (JP); Koji Kishi, Kobe (JP); Kazuaki Yamashita, Kobe (JP)

(73) Assignee: Sysmex Corporation, Hyogo (JP)

( * ) Notice: Subject to any disclaimer, the term of this patent is extended or adjusted under 35 U.S.C. 154(b) by 390 days.

(21) Appl. No.: 10/424,740

(22) Filed: Apr. 29, 2003

(65) Prior Publication Data

US 2003/0228316 A1    Dec. 11, 2003

(30) Foreign Application Priority Data

Apr. 30, 2002 (JP) .............................. 2002-129070

(51) Int. Cl.
*C12N 5/20* (2006.01)
*C07K 16/40* (2006.01)
*G01N 33/53* (2006.01)

(52) U.S. Cl. .................. 435/326; 435/975; 530/388.26

(58) Field of Classification Search ........... 530/388.26, 530/389.1; 435/975, 326
See application file for complete search history.

(56) References Cited

U.S. PATENT DOCUMENTS 6,440,710 B1 * 8/2002 Keinan et al. .............. 435/148
6,586,194 B1 * 7/2003 Shirahase et al. .......... 435/7.92

OTHER PUBLICATIONS

Thomure et al. Regulation of creatine kinase isoenzymes in human placenta during early, mid-, and late gestation. J Soc Gynecol Investig. Nov.-Dec. 1996;3(6):322-7.*
Schlattner et al. Divergent enzyme kinetics and structural properties of the two human mitochondrial creatine kinase isoenzymes. Biol Chem. Nov. 2000;381(11):1063-70.*
Harlow E, Lane D.. Antibodies a laboratory manual. Cold Spring Harbor, New York: Cold Spring Harbor Laboratory Press,pp. 141-149 and 151-155, 1989.*

* cited by examiner

*Primary Examiner*—Maher M. Haddad
(74) *Attorney, Agent, or Firm*—Sughrue Mion, PLLC (57) ABSTRACT

The object of the present invention is to provide a method for more accurately assaying the enzyme activities of mCK isozymes and a method for separately assaying the enzyme activities of CK isozymes by separately assaying the enzyme activities of ubiquitous mCK (umCK) and sarcomeric mCK (smCK). The above object is attained by an assay using an antibody that specifically recognizes umCK protein. In addition, other anti-mCK antibodies (e.g., anti-smCK antibody) and/or anti-human CK-M-inhibiting antibody can also be used. The above antibody is a polyclonal antibody or a monoclonal antibody. As a result of these antibodies, a monoclonal antibody (U1-1881) that is capable of specifically recognizing human umCK and is produced by a hybridoma having a deposition number of FERM BP-8342 is provided.

6 Claims, 3 Drawing Sheets

MITOCHONDRIAL CREATINE KINASE ANTIBODY

TECHNICAL FIELD

The present invention relates to a method for assaying the enzyme activities of creatine kinase (CK) isozymes that are assayed in the field of the clinical test, antibodies used for the assay, and a reagent (kit) for the assay.

BACKGROUND ART

The human CKs include four proteins encoded by different genes. Two proteins that are derived from the cytoplasm, and are called 'muscle type (M type)' and 'brain type (B type)' depending on their localization, and others that are derived from the mitochondria. CK isozymes derived from the cytoplasm are dimers consisting of M type and/or B type, and are classified as CK-MM, CK-MB, and CK-BB. Mitochondria CKs (mCKs) are octamers, and two kinds exist very stably, but they dissociates into dimers within a few minutes in the presence of a transient state-analogue complex consisting of creatine, Mg, ADP and nitrate. It is known that they gradually dissociate in the blood (Karin Fritz-Wolf et al., Nature, 361, 341–345 (1996)).

These isozymes migrate in the electrophoresis from the cathode side in the following order: mCK (octamer)>mCK (dimer)=CK-MM>CK-MB>CK-BB. The mCK (dimer) has a mobility equal to that of CK-MM, so that the former can be mis-identified as 'CK-MM' in the preserved blood. The macro CK bound to immunoglobulin also exits although it is not an isozyme. These can be identified from a zymogram by the mobility, the immunity counter current method, and so on.

The assay of CK and CK isozymes is widely used in the clinical test. CK-MB is important as a marker for the cardiac infarct among them. CK-MB is assayed by the EIA method, the immunity inhibition, the electrophoresis method, and so on. Although the EIA method permits specifically assaying only CK-MB, it requires a specially designed instrument, and has a problem in the promptness. The electrophoresis method requires a complex manipulation and skill, and a densitometer is necessary to obtain a ratio of CK-MB, i.e., the method also has a problem in the promptness. Although the immunity inhibition permits a rapid and simple assay when an automated analyzer is used, it is a fault that it lacks the specificity.

Under the present situation, however, it is required to diagnose the cardiac infarct at an early stage. Therefore, the immunity inhibition that permits the rapid and simple assay is widely used. In this method, the enzyme activity of CK-M subunit is inactivated using a specific antibody against the CK-M subunit ('anti-CK-M antibody'), and remaining CK-B subunit activity is assayed. By this method, CK-BB and mCK (dimer+octamer) as well as CK-MB are also assayed. Among these, little CK-BB is present in the blood, i,e,, negligible. Although diseases caused by the deviation of CK-BB include the brain contusion and the multiple organ failure, these cases are rare. Even in the serum of a healthy person, mCK is contained in an active amount nearly equal to CK-MB (Yoko Toyoda et al., Seibutsu Butsurikagaku, 41, 244 (1997); Tadashi Hoshino et al., Seibutsu Butsurikagaku, 42 (supplement) 2, 21 (1998)). In addition, in the cell necrosis such as liver disease and the malignant tumor, mCK is deviated, and the judgment of the result is disturbed. Recently, it was reported that mCK is deviated by the enteritis by rotavirus and the asphyxia neonatorum (Tadashi Hoshino et al, Rinsho Byori 46, Meeting Issue, 57 (1998); Fusae Kanemetsu et al, Rinsho Byori 46, Meeting Issue, 58 (1998). It was also reported that the presence of mCK affects CK-MB measurements by the enzyme inhibition method (Abstracts for 22nd Meeting of The Chiba Pref. Society for Clinical and Hygienic Tests 6_7 (February 2001). Then, a method was reported in which an antibody specific to mCK activity(anti-mCK antibody) was prepared and anti-mCK antibody together with anti-CK-M antibody was made to act to CK isozymes to inhibit CK-M subunit activity and mCK activity for more accurate assay of CK-MB (JP P2002-270A).

The mCK includes ubiquitous mCK (umCK) and sarcomeric mCK (smCK) isoforms. It was reported from the genetic analysis of mCK that amino acid sequences of human mCK, CK-M and CK-B are homologous one another at 62–66% and that amino acid sequences of umCK and smCK are homologous each other at 80% (J. Biol. Chem. 265: 6921–6927 (1998)). Isolating umCK and smCK and examining the properties of them revealed that umCK and smCK form dimer and octamer, respectively, and have slightly different pI values and that the octamer gave antigenicity at a similar level and was discriminated from the dimer (Fusae Kanemitsu et al., Rinsho Byori 47, Meeting Issue, 306 (1999)).

The relation between the deviation of mCK and diseases has been frequently reported very often as described above. The mCK is generally assayed by the agarose electrophoresis, and umCK and smCK behave similarly, so that both have been reported without distinguishing each other. Although an antibody having an anti-smCK activity was reported (JP P2002-270A), no report was published concerning anti-umCK antibody, and it was difficult to easily distinguish and analyze both.

DISCLOSURE OF THE INVENTION (Problem which the Invention Attempts to Solve)

It is an object of the present invention to provide a method for more accurately assaying mCK isozymes and a method for separately assaying CK isozymes by separately assaying the enzyme activities of umCK and smCK. Another object of the invention is to provide various mCK antibodies that can be used for the assay, in particular an antibody that specifically inhibiting the enzyme activity of umCK.

(Means for Solving the Above Problem)

As a result of investigations for achieving the above subjects, it was assumed that the majority of normal human mCK isozymes are umCK, so that it was considered that obtaining an antibody specifically inhibiting the enzyme activity of umCK make it easy to separately assay umCK and smCK. Therefore, examinations were carried out to successfully be able to prepare an antibody that specifically inhibits the enzyme activity of umCK to complete the present invention.

The present invention provides:

1. An anti-mCK antibody that inhibits an enzyme activity of ubiquitous mCK (umCK) among creatine kinase isozymes localized in mitochondria (mCK).
2. The antibody according to foregoing paragraph 1, wherein the antibody inhibits the enzyme activity of umCK at 60% or more.
3. The antibody according to foregoing paragraph 1, wherein the antibody is capable of inhibiting the enzyme activity of mCK down to such a level that an assay of CK isozymes other than mCK isozymes is not substantially affected.

4. The antibody according to foregoing paragraph 1, wherein the antibody is a monoclonal antibody.

5. A monoclonal antibody produced by a hybridoma having a deposition number FERM BP-8342.

6. A hybridoma having a deposition number FERM BP-8342.

7. A method for immunologically assaying mCK, comprising steps of providing a specimen; and treating the specimen with an antibody for inhibiting an enzyme activity of umCK.

8. The method according to foregoing paragraph 7, comprising a step of treating the specimen with an anti-mCK antibody for inhibiting an enzyme activity of sarcomeric mCK (smCK) among mCK isozymes.

9. The method according to foregoing paragraph 8, wherein the step of treating the specimen with the antibody for inhibiting the enzyme activity of umCK and the step of treating the specimen with the antibody for inhibiting the enzyme activity of smCK are carried out in one step.

10. A method for assaying CK isozymes, comprising steps of providing a specimen; and treating the specimen with an antibody for inhibiting an enzyme activity of umCK.

11. The method according to foregoing paragraph 10, the treating step is performed by treating the specimen with the antibody for inhibiting the enzyme activity of umCK and an antibody for inhibiting an enzyme activity of smCK.

12. The method according to foregoing paragraph 10, comprising a step of assaying an enzyme activity of CK in the specimen before the step of treating with the antibody, and a step of assaying a remaining enzyme activity after the step of treating with the antibody.

13. The method according to foregoing paragraph 10, comprising a step of treating the specimen with an anti-CK-M subunit antibody.

14. The method according to foregoing paragraph 13, wherein the step of treating the specimen with the antibody for inhibiting the enzyme activity of umCK and the step of treating the specimen with the anti-CK-M subunit antibody are carried out in one step.

15. The method according to foregoing paragraph 13, wherein the step of treating the specimen with the antibody for inhibiting the enzyme activity of umCK and the step of treating the specimen with the anti-CK-M subunit antibody are carried out in two steps.

16. The method according to foregoing paragraph 15, comprising steps of treating the specimen with the anti-CK-M subunit antibody; assaying a first remaining enzyme activity of the specimen; treating the specimen with the antibody for inhibiting the enzyme activity of umCK; and assaying a second remaining enzyme activity of the specimen.

17. A method for testing CK isozymes, comprising steps of assaying CK isozymes including a step of treating the specimen with an antibody for inhibiting an enzyme activity of umCK; and relating a result of assay with disease.

18. A reagent for assaying CK isozymes, comprising anti-mCK antibody for inhibiting an enzyme activity of umCK among mCK isozymes.

19. The reagent according to foregoing paragraph 18, comprising an anti-CK-M subunit antibody.

20. The reagent according to foregoing paragraph 19, comprising an anti-mCK antibody for inhibiting an enzyme activity of smCK among mCK isozymes.

21. A reagent kit for assaying CK isozymes, comprising a reagent including anti-mCK antibody for inhibiting an enzyme activity of umCK among mCK isozymes.

22. The reagent kit according to foregoing paragraph 21, comprising a reagent including an anti-CK-M subunit antibody.

23. The reagent kit according to foregoing paragraph 21, wherein the reagent including an anti-mCK antibody for inhibiting an enzyme activity of smCK among mCK isozymes.

DESCRIPTION OF SYMBOLS

—○—inhibition effect of enzyme activity of umCK
—△—inhibition effect of enzyme activity of smCK
—◆—inhibition effect of enzyme activity of CK-MM
—■—inhibition effect of enzyme activity of CK-BB

BEST MODE FOR CARRYING OUT THE INVENTION

The term 'enzyme activity of mCK' is used in the present invention to indicate the enzyme activity of umCK and/or the enzyme activity of smCK or the total enzyme activities of mCK including these activities.

The term 'anti-mCK antibody' is used in the present invention to indicate an antibody inhibiting the enzyme activity of mCK. The term 'an antibody inhibiting the enzyme activity of smCK' is used to indicate an antibody that specifically recognizes an smCK-type protein and specifically inhibits its enzyme activity. Similarly the term 'an antibody inhibiting the enzyme activity of umCK' is used to indicate an antibody that specifically recognizes a umCK-type protein and specifically inhibits its enzyme activity. Any antibody capable of inhibiting the enzyme activity of mCK down to a level that does not substantially affect the assay of CK isozymes other than mCK can be used for the antibody for separately assaying CK isozymes according to the present invention. The mCK is contained in the specimen at 5–20 U/L in many cases, and an antibody capable of inhibiting the enzyme activity of mCK at 80% or higher can be used for clinical tests without any problem. Such a system can be used which was prepared as to be substantially able to inhibit the enzyme activity of mCK at 80% or higher, for example, by combining an antibody that inhibits the enzyme activity of smCK with other antibodie(s) and/or by using a compound capable of inhibiting mCK even if an antibody that inhibits the enzyme activity of umCK ('anti-umCK antibody') has a low mCK-inhibiting ability when used singly. An antibody that inhibits the enzyme activity of umCK at 60% or more, preferably at 70% or more, more preferably at 90% or more, can be used for the anti-umCK antibody according to the present invention.

Although both polyclonal antibodies and monoclonal antibodies can be used for the antibody according to the present invention, the latter is preferable.

(Preparation of Antibody)

Antibodies according to the present invention can be ones derived from mouse as well as rat, hamster, rabbit, goat, and horse, preferably from mouse. The antibodies can be IgG as well as IgM, and so on.

Antibodies according to the present invention can be obtained by well-known immunological techniques, for example, from the serum of an animal immunized by using umCK protein as an antigen, preferably together with an adjuvant. Monoclonal antibodies and hybridomas producing the monoclonal antibodies can be prepared by fusing a B lymphocyte derived from an immunized animal with various myeloma cells, concretely by the method described below.

(Antigen Used for Preparing Antibody)

For the present invention, human or mammalian umCK is generally used as an antigen for preparing an antibody that has a specific affinity, for example to umCK, and inhibits its enzyme activity. In order to enhance the specificity, it is preferable to use an antibody specific to the species of the object for the measurement. For example, it is preferable to use human umCK as an antigen in case an antibody is prepared which has specific affinity to human umCK and specifically inhibits its enzyme activity. A umCK antibody can be obtained, for example, from a biological tissue through purification or by a genetic engineering technique. Antigens are commercially available, for example, from Institute of Cell Biology, Swiss Federal Institute of Technology (ETH).

(Immunization Method)

Purified umCK protein, umCK protein expressed by a genetic engineering technique based on its amino acid sequence or a partial peptide thereof is dissolved or suspended in an appropriate buffer such as phosphate buffer solution (PBS) to use as an antigen solution, which can be usually prepared so as to contain an antigen at 50–500 µg/mL or so. Peptide antigens or the like that have low antigenicity when used singly can be used after linking to an appropriate carrier protein such as albumin and keyhole limpet hemocyanin (KLH). Animals immunized with the antigen are mouse, rat, hamster, horse, goat, and rabbit, preferably mouse, in particular BALB/c mouse.

In order to enhance the response of an animal to be immunized to the antigen, the antigen solution can be administered as a mixture with an adjuvant. Acceptable adjuvants include Freund complete adjuvant (FCA), Freund incomplete adjuvant (FIA), Ribi (MPL), Ribi (TDM), Ribi (MPL+TDM), *Boredetella pertussis* vaccine, muramyl dipeptide (MDP), aluminum adjuvant (ALUM), and a combination of these. It is particularly preferable to use FCA for the first immunization and to use FIA or Ribi for the additional immunization as an adjuvant.

The immunization method is variable depending on the kind of the antigen to use and the presence or absence of adjuvant to mix with respect to injection site and schedule. For example, in case mouse is used as the animal to immunize, 0.05–1 mL of an adjuvant-antigen mixture (antigen 10–200 µg) is injected intraperitoneally, hypodermically, intramuscularly or intravenously (tail), and additional immunization is carried out one to four times every about 4–21 days after the first immunization, and the final immunization is carried out after about 1–4 week(s) thereafter. It is also possible to administer a solution containing the antigen in a large amount by the intraperitoneal injection without adjuvant. The antibody titre is assayed by collecting blood about 5–10 days after the additional immunization by the normal method described later. Splenic cells are collected from the immunized animal about 3–5 days after the last immunization to obtain antibody-producing cells.

(Preparation of Monoclonal Antibody)

A monoclonal antibody (MoAb) can be prepared according, for example, to Kohler and Milstein, Nature 256, 495–497, 1975. Myeloma cells used are derived from mouse, rat, and human. For example, mouse myeloma P3X63-Ag8, P3X63-Ag8-U1, P3NS1-Ag4, SP2/o-Ag14, and P3X63-Ag8-653 are used. Some myeloma cells produce the immunoglobulin light chain. If this chain is used as an object for fusion, the immunoglobulin heavy chain produced by antibody-producing cells and the light chain can be linked at random, so that it is preferable to use myeloma cells that do not produce immunoglobulin light chain such as P3X63-Ag8-653 and SP2/o-Ag14. It is preferable that the antibody-producing cell and the myeloma cell are derived from an allogenic animal, in particular, that of the same parentage. Myeloma cells can be preserved according to the well-known method, for example, by subculturing in a general medium to which horse, rabbit or bovine fetal serum was added, followed by lyophilizing the obtained culture. It is preferable to use cells at a logarithmic phase for the cell fusion.

Methods for preparing a hybridoma by fusing an antibody-producing cell with a myeloma cell include a method using polyethylene glycol (PEG), a method using Sendai virus, and a method using an electrofusion device. In case the PEG method is used, splenic cells and myeloma cells are suspended in an appropriate medium or buffer containing about 30–60% PEG (average molecular weight of 1,000–6,000) at a ratio from (1:1) to (10:1), preferably from (5:1) to (10:1), and are incubated at about 25–37° C., pH 6–8 for about 30 sec to 3 min. After the incubation, the obtained cells are washed to remove PEG, and are resuspended in a medium, and are inoculated on a microtitre plate to continue the culture.

Cells after the fusion procedure are culture in a selective medium to select a hybridoma. The selective medium is a medium that allows parent cells to sterilize and fused cells to grow. Hypoxanthine-Aminopterin-Thymidine (HAT) medium is usually as the selective medium. A hybridoma is selected by exchanging a part, preferably a half, of the medium with the fresh selective medium usually 1–7 day(s) after the fusion procedure, followed by repeating similar medium-exchanging procedures every 2–3 days. Colonies of hybridomas in wells are observed by the microscopy.

Whether a growing hybridoma is producing a desired antibody or not can be determined by collecting the culture supernatant, followed by assaying an antibody titre by a well-known method. For example, adding serially diluted supernatant to an immobilized antigen protein for reaction and then adding a second antibody (e.g., anti-globulin antibody, anti-IgG antibody, anti-IgM antibody) labelled with a fluorescent material, an enzyme, or a radio isotope (RI) to the obtained mixture for reaction permit detecting an antibody produced in the supernatant and assaying an antibody titre. In case the antigen is an enzyme, reacting the enzyme with the supernatant and then assaying the enzyme activity using an appropriate substrate permit detecting an antibody and assaying an antibody titre. Thus, the culture supernatant in each well is screened, and a hybridoma producing an appropriate antibody is obtained.

In addition, a single clone is isolated by the limit dilution method, the soft agar method, or the method using a fluorescence-excited cell sorter. For example, in the case of the limit dilution method, serially diluting a colony of a hybridoma with a medium so that one well can contain one cell or so and culturing cells permit isolating a hybridoma clone producing the objective antibody. Freezing the obtained antibody-producing hybridoma clone in the presence of about 10%(v/v) cryoprotective agent such as dimethyl sulfoxide (DMSO) and glycerin and preserving the frozen cells at −70 to −196° C. permit preserving the cells for about half a year or more or almost permanently. When needed, cells are rapidly thawed in an incubator at 37° C. or so. It is preferable to use the cells after adequately removing the cryoprotective agent that can be cytotoxic.

The immunoglobulin subclass of the antibody produced by the hybridoma can be determined by culturing the hybridoma under general conditions, followed by analyzing an antibody secreted into the culture supernatant by a commercially available kit for determining the antibody class/subclass.

MoAb can be obtained from a hybridoma, for example, from the mouse peritoneal fluid to which the hybridoma was transplanted or from culture supernatant of a cell culture, depending on the amount necessary or properties of the hybridoma. In case a hybridoma that can proliferate in the mouse intraperitoneal cavity is used, a high concentration (several mg/mL) of MoAb can be obtained from the peritoneal fluid of a cell culture. A hybridoma that can not proliferate in vivo is obtained from a culture supernatant. Although MoAb is obtained by the cell culture at a lower yield than that in vivo, the antibody is less contaminated with immunoglobulin and impurities contained in the mouse peritoneal fluid, and the antibody can be easily purified, i.e., it is advantageous.

In case an antibody is obtained from the mouse peritoneal cavity to which a hybridoma was transplanted, peritoneal fluid stored is collected about 1–3 week(s) after hybridomas (more than about 10⁶ cells) are transplanted into the peritoneal cavity of BALB/c mouse to which an immunosuppressive agent such as pristane (2,6,10,14-tetramethylpentadecane) had been administered. In the case of heterologous hybridoma (e.g., one derived from mouse and rat), nude mouse and irradiated mouse are preferably used.

On the other hand, in case an antibody is collected from the supernatant of a cell culture, the hybridoma is cultured by a culture method such as the high-density culture method and the spinner flask culture method as well as the stationary culture method that is used for maintaining cells, and culture supernatant containing an antibody is obtained. The serum contained in the culture liquid contains impurities such as other antibodies and albumin and can make it complex to purify the antibody complex. Therefore, it is desirable to reduce the amount of serum for adding to the culture liquid. It is more preferable to adapt a hybridoma to a serum-free medium according to the usual method to culture with a serum-free medium. Culturing with a serum-free medium make it easy to purify the antibody.

MoAb can be easily purified from peritoneal fluid or culture supernatant by the well-known method such as the fractionation by salting-out with ammonium sulfate or sodium sulfate, the polyethylene glycol fractionation, the ethanol fractionation, the DEAE ion-exchange chromatography, and the gel filtration, which has been known as methods for purifying immunoglobulins.

In case MoAb is mouse IgG, the antibody can be simply purified by the affinity chromatography using protein A-bound carrier or anti-mouse immunoglobulin-bound carrier.

In the present invention, MoAb capable of specifically recognizing and inhibiting umCK was prepared by the above technique using human umCK (Institute of Cell Biology, Lot. No. ETH 010122) as the antigen. Said antibody is derived from mouse, is an IgG class antibody, and was obtained by screening one capable of specifically inhibiting the enzyme activity of umCK at 60% or more, preferably 80% or more, more preferably 90% or more. The hybridoma which produced the antibody, was deposited in International Patent Organism Depositary, National Institute of Advanced Industrial Science and Technology(formerly National Institute of Bioscience and Human-Technology, Agency of Industrial Science and Technology, Ministry of International Trade and Industry) on Mar. 13, 2002 with a deposition number FERM P-18760 and the antibody was named UI-1881. The hybridoma of FERM P-18760 was transferred from domestic deposit to deposit under the Budapest Treaty on Mar. 24, 2003 with a deposition number FERM BP-8342. An antibody according to the present invention is not limited to the example. An antibody that specifically recognizes human umCK and is capable of specifically inhibiting its enzyme activity serves as the antibody according to the present invention. An anti-umCK antibody according to the present invention can be used singly or, if necessary, together with anti-mCK antibodies, for example, ones having different recognition sites when used for inhibiting the enzyme activity of mCK. It can be used singly or, if necessary, together with anti-umCK antibodies, for example, ones having different recognition sites also when used for inhibiting the enzyme activity of umCK.

An antibody capable of specifically recognizing and inhibiting sarcomeric mCK (smCK) ('anti-smCK antibody') can also be used for the assay method according to the present invention. A hybridoma which produced a MoAb (JP P2002-270A) deposited at National Institute of Bioscience and Human-Technology, Agency of Industrial Science and Technology, Ministry of International Trade and Industry on Apr. 13, 2000 with a deposition number FERM BP-7133 and the MoAb was named mCKI-578 can be used singly or in a combination as an example of anti-smCK antibody.

Therefore, using the anti-umCK antibody and anti-smCK antibody singly or in a combination permits selectively inhibiting the enzyme activity of mCK, umCK or smCK in a specimen. In addition, using it together with an antibody that selectively removes CK-M subunit permits separately assaying enzyme activities of CK isozymes (CK-MB, CK-MM, CK-BB and mCK), in particular, umCK and/or smCK.

(Method for Immunological Assay)

An anti-umCK antibody and an anti-smCK antibody according to the present invention can be used for the EIA method, the RIA method, the immune agglutination, and all other procedures for measurement that are enabled using an antibody. In this case, for example, an antibody immobilized on a carrier, a labelling antibody, and other reagents can be appropriately selected according to an assaying object, and can be used under optimal conditions. For example, assaying by an immunological technique separately using anti-umCK antibody and anti-smCK antibody permits separately assaying umCK and smCK that had not be able to be discriminated by the electrophoresis so far.

(Method for Assaying Isozyme by Immunological Inhabitation)

The basic principle of a method for assaying CK isozyme utilizes a method for selectively assaying the enzyme activity of a CK isozyme by the immunological inhibition. In general, the CK-MB activity is assayed by this method as follows: CK-MB activity is assayed by inhibiting M subunit activity (about a half of the MB activity is inhibited) in CK-MM and MB in a specimen using a human CK-M subunit-specific active antibody, followed by doubling the remaining B subunit activity. The CK-MB activity is assayed by assaying NADPH by forming ATP by the left-directed reaction of Eq.1, consuming the formed ATP with hexokinase (HK) by Eq.2(top), followed by forming NADPH with glucose-6-phosphate dehydrogenase (G-6-PDH) by Eq.2(bottom).

In the above method for assaying CK-MB, the anti-CK-M antibody and the anti-umCK antibody and/or the anti-smCK antibody can be used for treating a specimen for assay at one step, for example, by adding the above antibodies to the enzyme solution for assay. It is also possible to treat the specimen by adding the anti-umCK antibody and/or the anti-smCK antibody to a substrate solution and by adding the anti-CK-M antibody to the enzyme solution for assay, i.e., in separate steps. In case the isozyme for assaying its activity is CK-MB, it is simple to treat a specimen with the anti-CK-M antibody and the anti-mCK antibody (anti-umCK antibody and/or anti-smCK antibody) in one step.

The present invention also provides a method for assaying mCK characterized by selectively removing mCK enzyme activity by treating a specimen with anti-umCK antibody and/or anti-smCK antibody. The present invention also provides a method for assaying umCK or smCK characterized by selectively removing an enzyme activity of umCK or smCK by treating a specimen with anti-umCK antibody or anti-smCK antibody. In the method for assaying mCK, umCK, or smCK according to the present invention, assaying the activity of creatine kinase including mCK in a specimen and the activity of creatine kinase other than mCK using the above anti-umCK antibody and anti-smCK antibody according to the present invention and calculating a difference between the obtained two measurements permit determining each activity of mCK, umCK or smCK. In this assay, the activity of creatine kinase including mCK in a specimen and the activity of creatine kinase other than mCK using the above anti-mCK antibody according to the present invention can be assayed using an assay kit containing anti-CK-M antibody or an assay kit not containing it as long as the assay kit used for the two assays contain the same amount of anti-OK-M antibody.

For example, assaying the activity of total CKs in a specimen, assaying the activity in the presence of the anti-umCK antibody and/or anti-smCK antibody according to the present invention, and calculating the difference between the two measurements permit determining the mCK activity, in particular, umCK activity and/or smCK activity.

Treating a specimen with anti-CK-M antibody, inhibiting about a half of CK-MM activity and CK-MB activity, assaying ½CK-MB+mCK enzyme activity to give measurement A, adding anti-umCK antibody and/or anti-smCK antibody according to the present invention, and assaying ½CK-MB enzyme activity to give measurement B permit simultaneously, simply and rapidly assaying mCK or umCK or smCK as well as CK-MB activity using a single specimen. Doubling measurement B permits determining CK-MB activity, and determining the difference between measurement A and measurement B permits assaying mCK or umCK or smCK activity.

For example, separately assaying the activity of CK including mCK and the activity of CK other than mCK in a specimen and determining the difference between the obtained two measurements permit determining mCK activity. For example, assaying each activity using kit A and kit B as described below and determining the difference between the two obtained measurements permit determining mCK activity. At this time, using CK-MB activity assay kit that contains kit A and anti-CK-M antibody permits assaying mCK activity as well as CK-MB activity.

Kit A: Reagent kit for assaying total CK activity including mCK in a specimen

Kit B: Reagent kit, for assaying CK activity other than mCK (in particular umCK and/or smCK activity) in a specimen, prepared by adding anti-umCK antibody and/or anti-smCK antibody to kit A.

In addition, assaying the activity of creatine kinase other than mCK (in particular umCK and/or smCK activity) in a specimen using anti-umCK antibody and/or anti-smCK antibody to give measurement C, assaying the activity of CK other than mCK, CK-MM, and ½CK-MB using anti-CK-M antibody and anti-umCK antibody and/or anti-smCK antibody to give measurement D, and determining the difference between measurement C and a value obtained by doubling measure D permit determining CK-MM activity.

There is no special limitation in the specimen assayed by the method according to the present invention. The present invention is applicable to the methods and specimens which are usually used in the field of clinical test and in which CK isozymes are assayed. The abnormal appearance of mCK among active fractions of CK isozymes had been observed in cardio-respiratory arrest, injury, infant diarrhea, carcinoma, liver cirrhosis, and congestive heart failure (Kensa to Gijutsu vol.28, no.13, p.1499–1504 (2000). The assay method according to the present invention permits diagnosing the above diseases and detecting the abnormal appearance of umCK and smCK and determining their ratios although umCK and smCK were not discriminated because of their similar behaviors in the electrophoresis. Thus, the assay method according to the present invention provides a method for testing umCK and/or smCK that serve(s) as index(es) for each disease.

The present invention also provides a reagent (kit) for assaying the activity of a CK isozyme consisting of reagent(s) necessary for the method for assaying CK isozymes, the method for assaying CK-MB, and the method for assaying mCK according to the present invention. The reagent (kit) for assaying the activity of a CK isozyme according to the present invention contains anti-mCK enzyme activity-inhibiting MoAb singly or together with other ingredient(s). Although reagent (kit) for assaying the total activity of CK and/or reagent (kit) for assaying CK-MB that is/are used for biochemically diagnosing the acute myocardial infarction can be used as a part for the reagent (kit) according to the present invention, other reagent (kit) can also be used.

EXAMPLES

The following examples are not given to limit the scope of the present invention, but to concretely describe the present invention.

Example 1

Preparation of Hybridoma that Produces Monoclonal Antibody (MoAb)

(1) Preparation of Immunogen (Antigen)

Human umCK (Institute of Cell Biology, Lot No.ETH010122) was used as an antigen for the present invention.

(2) Animal to Immunize 5 to 8-week-old inbred BALB/c female mice were bred feeding standard pellets and arbitrarily supplying water in an animal-breeding chamber (23±1° C.; humidity, 70%).

(3) Immunizing Method

Purified human umCK (antigen) prepared in (1) was dissolved in PBS to give a concentration of 100 μg/0.5 mL, and the obtained solution was mixed with the same volume (0.5 mL) of Freund's complete adjuvant (Difco) to give a homogenate. The homogenized antigen solution was administered into the peritoneal cavity of four 5-week-old female BALB/c mice by a dose of 200μL per mouse. Every two weeks, the above antigen prepared with Ribi adjuvant to give a concentration of 100 μg/mL was four times administered to mice by a dose of 20 μg per mouse. After one month, the above antigen prepared with Ribi adjuvant to give a concentration of 100 μg/mL was administered for additional immunization, and antibody titres of the mice were assayed. After 2 weeks, a 100 μg/mL purified human mCK (antigen) solution in PBS was administered to mice giving high antibody titres by the intravenous injection for the final immunization.

(4) Antibody Titre Assay

Since the initiation of the immunization, a small amount of whole blood was periodically collected from the mouse eyeground retina, and the serum was separated, and an antibody titre against umCK was assayed by the umCK enzyme activity antibody method.

25 μL of an antibody solution prepared by 10–1,000 folds diluting antiserum of each mouse with PBS and 25 μL of umCK enzyme solution (200U/L) were added to 96-well microtitre plate, and the plate was incubated at room temperature for 10 min, and 100 μL of an enzyme reagent [100 mM imidazole, 2 mM EDTA, 10 mM magnesium acetate, 2 mM adenosine-5'-diphosphoric acid (ADP), 5 mM adenosine-5'-monophophoric acid (AMP), 40M P1P5, P5-di(adenosine-5')5-phosphoric acid (5P5A), 30 mM 1-thioglycerol, 28 mM D-glucose, 2 mM NADP, 3 U/mL HK, 2 U/mL glucose-6-phosphate dehydrogenase, 30 mM disodium creatine phosphate, 0.3 mg/mL Nitro-Blue tetrazolium chloride, 0.6 U/mL diapholase, pH6.6] was added to the 96-well titre plate, and the plate was incubated at 37° C. for 10 min.

Then, absorbance at 570 nm was measured, with a reagent blank serving as the control, with a system to which non-immunized mouse serum was added instead of the antiserum serving as the negative control.

TABLE 1

| Immunity | Day | Mouse No. 1 | Mouse No. 2 | Mouse No. 3 |
|---|---|---|---|---|
| 1 | 0 | 0 | 0 | 0 |
| 2 | 35 | nd | nd | nd |
| 3 | 56 | 7 | 24 | 57 |
| 4 | 91 | 1 | 25 | 37 |
|   | 102 | 22 | 34 | 51 |
| 5 | 116 | 35 | 24 | 53 |
|   | 129 | 18 | 39 | 48 |
|   | 137 | 32 | 37 | 52 |
| 6 | 150 | 25 | 38 | 36 |
| 7 | 167 | 0 | 43 | 41 |

If umCK enzyme activity-inhibiting specific antibody is produced in the blood, the enzyme activity of umCK is inhibited, and the substrate reaction is suppressed to reduce the change in the absorbance. The presence of umCK enzyme activity-inhibiting specific antibody can be detected by the obtained absorbance, so that the inhibition of the umCK enzyme activity was detected in each mouse as shown in Table 1.

(5) Cell for Cell Fusion

Three days after the final immunization, the spleen was removed from BALB/c mouse, and spleen cells were suspended in EMEM medium to give a suspension of spleen cells. The spleen cells were four times washed with fresh EMEM medium, and the cell number was counted to be $7.0 \times 10^8$. 8-Azaguanine (2-amino-6-oxy-8-azapurine)-resistant myeloma cell line (P3X63-Ag8-653, 'X63 cell') derived from BALB/c mouse was used as the parent cell line for the cell fusion. X63 cells were subcultured with RPMI-1640 medium (containing 8-azaguanine at 20 μg/mL) containing inactivated fetal calf serum (FCS) at 10%. The cells were cultured with RPMI-1640 medium that contained 10% FCS but does not contain 8-azaguanine since three days before the cell fusion, and cells at a logarithmic phase were used for the cell fusion. X63 cells were three times washed with RPMI-1640 medium, and the cell number was counted to show that the sample contains $7 \times 10^7$ cells.

Polyethylene glycol 4000 was dissolved in RPMI-1640 medium to give a concentration of 50%(w/v), and the above spleen cells and X63 cells were mixed each other to give a cell number ratio of 10:1, and the cell fusion was carried out according to the method described by Köhler, G. J. F. and Milstein, C. (Nature 256, 495–497 (1975); Eur. J. Immunol. 6, 511–519 (1976)).

Thereafter, spleen cells were suspended in HAT selective medium which was prepared by adding 10% FCS to RPMI-1640 and contains $1 \times 10^{-4}$ M hypoxanthine, $4 \times 10^{-7}$ M aminopterin and $1.6 \times 10^{-5}$ M thymidine (HAT) to give a population density of $2.0 \times 10^6$ cells/mL. Next, 50 μL portions of the cell suspension was added to each well of a 96-well microtitre plate, and the resultant plate was incubated at a temperature of 37° C., a relative humidity of 95%, a $CO_2$ concentration of 8%. One day and two days after the initiation of the incubation, one drop of HAT selective medium was added to each well. Seven days and 9 days after the initiation of the incubation, two drops of HAT selective medium were added to each well, and the resultant plate was further incubated. Thereafter, the cells were proliferated is a medium not containing HAT for about 10 days to 2 weeks, and the proliferated hybridomas were identified with a selective medium.

(6) Screening

Among the hybridomas thus obtained, a strain that produces an antibody (anti-human umCK MoAb) having an ability of inhibiting the enzyme activity of human umCK is selected by the method below.

After 25 μL of hybridoma culture supernatant and 25 μL of human umCK enzyme solution (200U/L) were added to a 96-well microtitre plate, and the resultant plate was incubated at room temperature for 10 min, and 200 μL of an enzyme reagent [100 mM imidazole, 2 mM EDTA, 10 mM magnesium acetate, 2 mM adenosine-5'-diphosphoric acid (ADP), 5 mM adenosine-5'-monophophoric acid (AMP), 40 μM P1, P5-di(adenosine-5')5-phosphoric acid (AP5A), 30 mM 1-thioglycerol, 28 mM D-glucose, 2 mM NADP, 3 U/mL HK, 2 U/mL glucose-6-phosphate dehydrogenase, 30 mM disodium creatine phosphate, 0.3 mg/mL Nitro-Blue tetrazolium chloride, 0.6 U/mL diapholase, pH6.6] was added to the 96-well titre plate, and the plate was incubated at 37° C. for 10 min. Then, absorbance at 570 nm was measured, with a reagent blank serving as the control, with a system to which only culture liquid was added instead of the hybridoma culture supernatant serving as the negative control. Obtained absorbance permits identifying a hybridoma that produces anti-human umCK MoAb.

Screening 2,496 wells of 96-well microtitre plates in which the hybridoma proliferated permitted identifying hybridomas that produce anti-human umCK MoAb in 7 wells.

Experimental Example 1

Enzyme Inhibition Specificity of Culture Supernatant

With respect to culture supernatant of hybridoma-producing cells in 7 wells found by the above screening, each enzyme activity inhibition was determined using human umCK, human smCK, human CK-MM, human CK-BB or human CK-MB to confirm the specificity against a human CK isozyme, with MoAb of mCKI-578 (JP P2002-270A) produced by a hybridoma having the deposition number FERM BP-7133 being a control.

Figure 1:
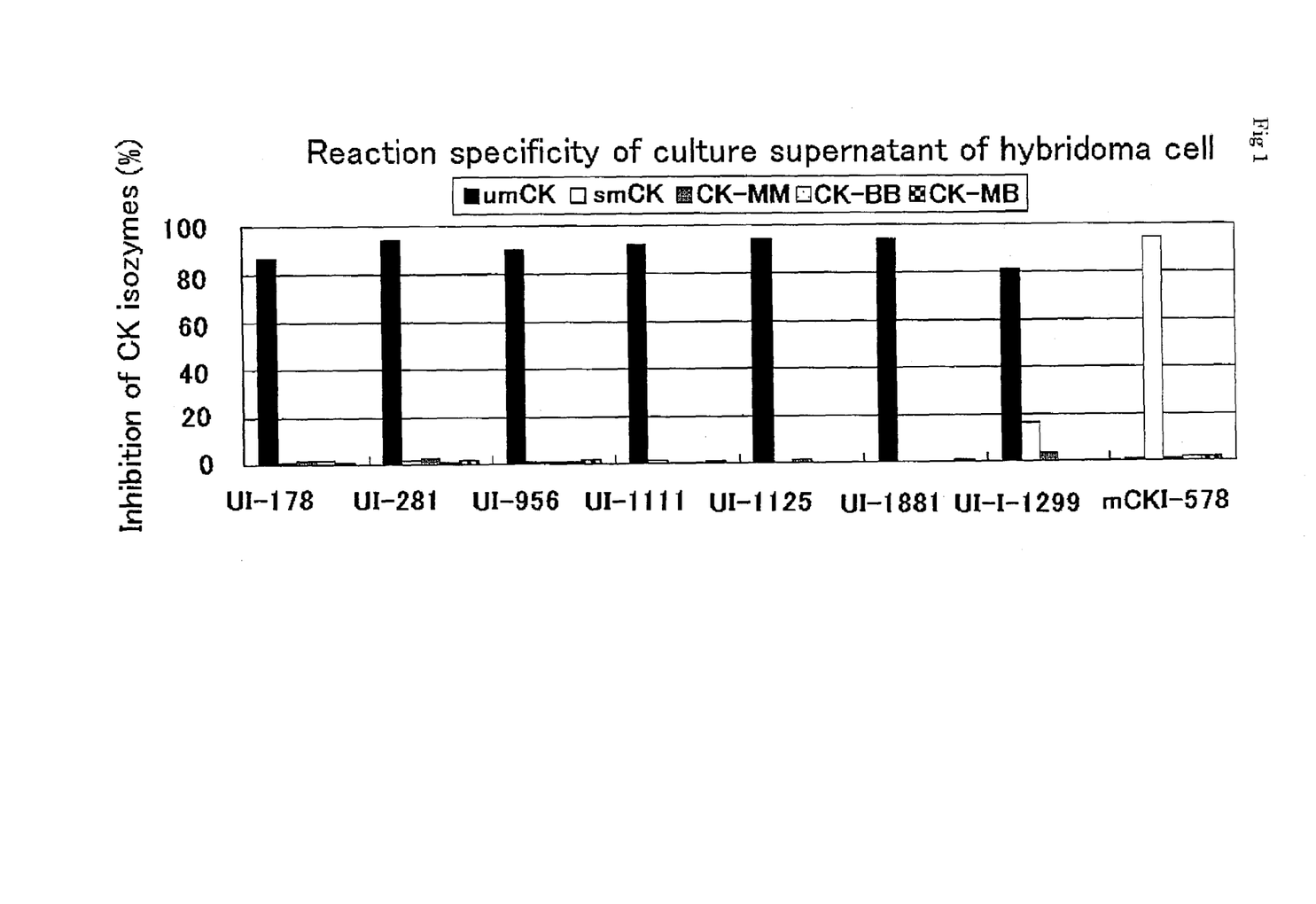
FIG. 1 illustrates abilities of a hybridoma culture supernatant of inhibiting enzyme activities of isozymes (Experimental example 1).

The result is shown in FIG. 1. The supernatants of clones UI-178, UI-281, UI-956, UI-1111, UI-1125, UI-1881 and UI-1-1299 inhibited the enzyme activity of umCK at 82% or more, but did not inhibit enzyme activities of smCK, CK-MM, CK-BB, and CK-MB at all. The supernatant of UI-1881 inhibited the enzyme activity of umCK at 94%. On the other hand, mCKI-578 inhibited the enzyme activity of smCK at 94%, but did not inhibit the enzyme activities of umCK or other isozymes.

Experimental Example 2

Establishment of MoAb-Producing Hybridoma Cell Line (Cloning)

Each of hybridomas in seven wells found by the above screening was isolated by the limit dilution method, and a hybridoma cell that produces MoAb stably inhibiting the enzyme activity of mCK was isolated as a clone, which was deposited in National Institute of Bioscience and Human-Technology, Agency of Industrial Science and Technology, Ministry of International Trade and Industry with the deposition number FERM BP-8342.

Experimental Example 3

Identification of Mouse Immunoglobulin Subclass

The mouse immunoglobulin subclass of MoAb (UI-1881) produced by FERM BP-8342 cells was identified using a MONOAb typing kit (Zymed) to found that UI-1881 is immunoglobulin G (IgG2b, κ).

Experimental Example 4

Specificity of UI-1881 to Human CK Isozymes

In order to examine the specificity of UI-1881 to human CK isozymes, the inhibition of enzyme activities was determined with human umCKm, human smCK, human CK-MM, human CK-BB, and human CK-MB. mCKI-578 (anti-smCK MoAb) was examined as a control.

Figure 2:
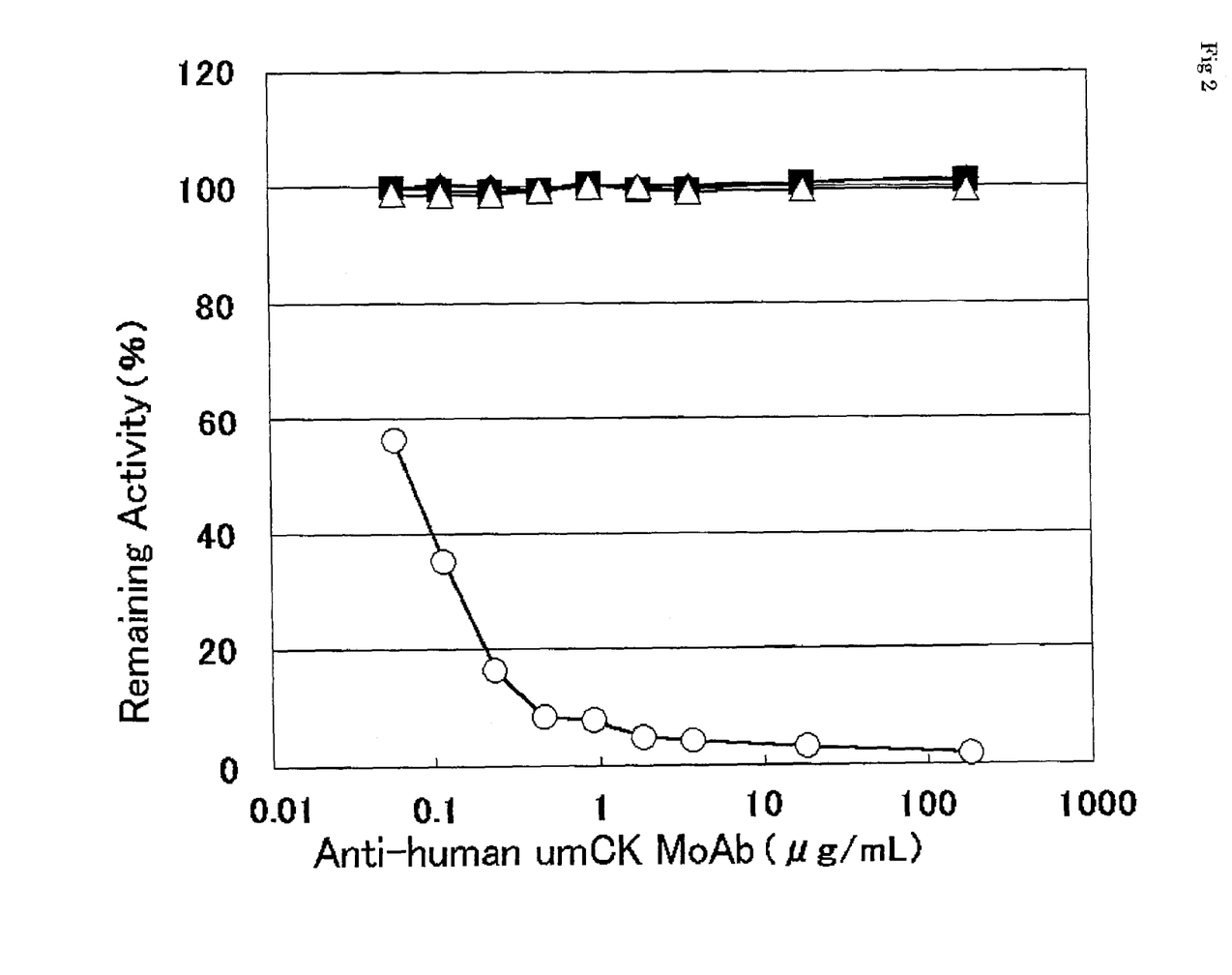
FIG. 2 illustrates abilities of anti-umCK monoclonal antibody (UI-1881) of inhibiting enzyme activities (Experimental example 4).
Figure 3:
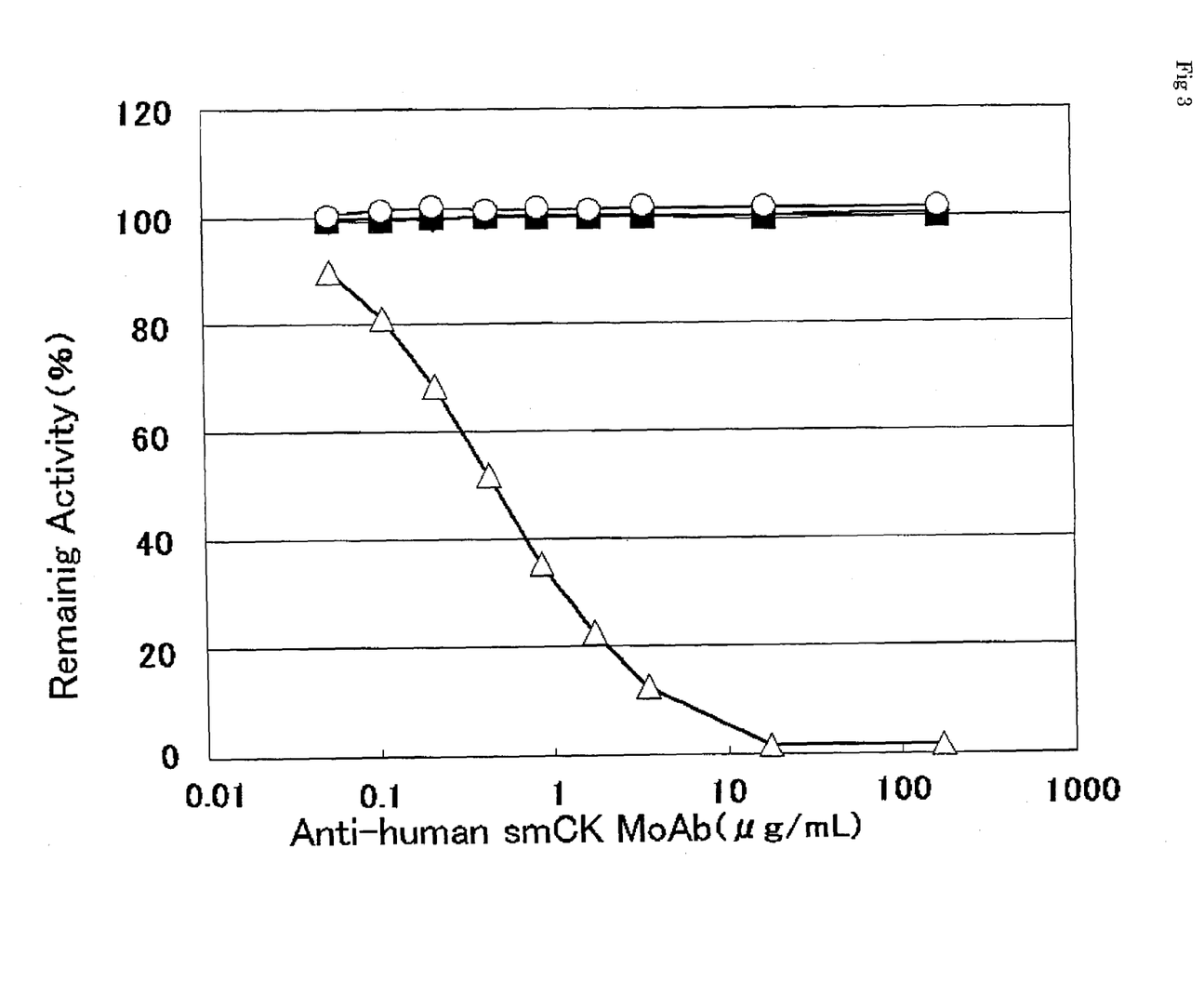
FIG. 3 illustrates abilities of anti-smCK monoclonal antibody (mCKI-578) of inhibiting enzyme activities (Experimental example 4).

Results were illustrated in FIGS. 2 and 3. UI-1881 inhibited the enzyme activity of umCK at about 90%, but did not inhibit the enzyme activities of smCK, CK-MM, CK-BB or CK-MB at all. On the other hand, mCKI-578 inhibited the enzyme activity of smCK at about 90%, but did not inhibit the enzyme activities of umCK, CK-MM, CK-BB or CK-MB at all.

INDUSTRIAL APPLICABILITY

As described above, the antibodies according to the present invention specifically inhibited the enzyme activity of umCK, but did not inhibit the activities of other isozymes. On the other hand, anti-smCK antibody specifically inhibited the enzyme activity of smCK, but did not inhibit the activities of other isozymes. Using these antibodies in a combination permits separately assaying isozymes in a specimen. Furthermore, separately assaying umCK and smCK permits detecting the abnormal appearance of these and determining their ratio. Investigating the relation between these data of clinical test and diseases caused by those enzymes permits diagnosing and treating those diseases at an early stage.

What is claimed is:

1. A monoclonal antibody produced by a hybridoma having a deposition number FERM BP-8342.

2. A hybridoma having a deposition number FERM BP-8342.

3. A reagent for assaying creatine kinase isozymes, comprising: an anti-mitochondria creatine kinase monoclonal antibody that inhibits an enzyme activity of ubiquitous mitochondria creatine kinase and does not inhibit enzyme activities of sarcomeric mitochondria creatine kinase, creatine kinase MM, creatine kinase BB and creatine kinase MB, and an anti-creatine kinase M subunit antibody which inhibits an enzyme activity of creatine kinase M subunit.

4. The reagent according to claim 3, comprising a second anti-mitochondria creatine kinase monoclonal antibody that inhibits an enzyme activity of sarcomeric mitochondria creatine kinase and does not inhibit enzyme activities of ubiquitous mitochondria creatine kinase, creatine kinase MM, creatine kinase BB and creatine kinase MB.

5. A reagent kit for assaying creatine kinase isozymes, comprising:

a first reagent including an anti-mitochondria creatine kinase monoclonal antibody that inhibits an enzyme activity of ubiquitous mitochondria creatine kinase and does not inhibit enzyme activities of sarcomeric mitochondria creatine kinase, creatine kinase MM, creatine kinase BB and creatine kinase MB, and a second reagent including an anti-creatine kinase M subunit antibody which inhibits an enzyme activity of creatine kinase M subunit.

6. The reagent kit according to claim 5, wherein the first reagent includes a second anti-mitochondria creatine kinase monoclonal antibody that inhibits an enzyme activity of sarcomeric mitochondria creatine kinase and does not inhibit enzyme activities of ubiquitous mitochondria creatine kinase, creatine kinase MM, creatine kinase BB and creatine kinase MB.

* * * * *